United States Patent [19]

Portenhauser et al.

[11] Patent Number: 4,701,417

[45] Date of Patent: Oct. 20, 1987

[54] CONTROL OR CALIBRATION SERUM FOR LIPID DIAGNOSIS

[75] Inventors: Rudolf Portenhauser, Tutzing; Knut Bartl, Wilzhofen, both of Fed. Rep. of Germany

[73] Assignee: Boehringer Mannheim GmbH, Mannheim, Fed. Rep. of Germany

[21] Appl. No.: 800,460

[22] Filed: Nov. 21, 1985

[30] Foreign Application Priority Data

Dec. 10, 1984 [DE] Fed. Rep. of Germany ....... 3445010

[51] Int. Cl.$^4$ ............................................. G01N 31/00
[52] U.S. Cl. ...................................... 436/13; 436/16; 436/18
[58] Field of Search ...................... 436/8–16

[56] References Cited

U.S. PATENT DOCUMENTS

| | | |
|---|---|---|
| 3,955,925 | 5/1976 | Proksch et al. .................. 436/14 |
| 4,011,045 | 3/1977 | Bonderman ...................... 436/13 |
| 4,039,285 | 8/1977 | Teipel ................................ 436/13 |
| 4,147,606 | 4/1979 | Golias ................................ 436/13 |
| 4,210,557 | 7/1980 | Handscuh .......................... 436/13 |
| 4,216,117 | 8/1980 | Proksch et al. .................. 436/13 |
| 4,226,713 | 10/1980 | Goldberg ........................ 436/13 |
| 4,290,774 | 9/1981 | Girgis et al. .................... 436/13 |
| 4,474,887 | 10/1984 | Maier et al. .................... 436/13 |
| 4,486,531 | 12/1984 | Ziegenhorn et al. .......... 436/13 |

*Primary Examiner*—Stephen C. Bentley
*Assistant Examiner*—T. J. Wallen
*Attorney, Agent, or Firm*—Felfe & Lynch

[57] ABSTRACT

The present invention provides a control or calibration serum for lipid diagnosis, wherein it contains the parameters relevant for lipid diagnosis in the normal or pathological concentration range in a single storage-stable form.

The present invention also provides processes for the preparation of this control or calibration serum.

9 Claims, No Drawings

CONTROL OR CALIBRATION SERUM FOR LIPID DIAGNOSIS

The present invention is concerned with a control and calibration serum which contains the parameters relevant for lipid diagnosis in a single, storage-stable form, as well as with a process for the preparation thereof.

Recent biochemical knowledge has contributed substantially to the elucidation of disturbances of the fat and protein metabolism. A more precise lipoprotein analysis permits correlations between the concentration of individual parameters and of the probability of coronary diseases or of the risk of the occurrence of an infarct. In this connection, the determination of total cholesterol, HDL cholesterol and LDL cholesterol have achieved especial importance. However, the determination of other parameters, such as triglycerides and apolipoproteins A1, A2 and B are also of importance.

For the control of the accuracy and precision of methods of determination and for the calibration of automatic analysers, there are usually employed control sera or calibration sera which contain the parameter to be determined in known and precisely fixed concentrations. There is a difference between special control sera, which serve for the control or for the calibration of quite definite parameters or of a limited and usually related group of parameters, and so-called universal control sera which can be used for the control or calibration of, as far as possible, all conventional parameters according to all methods of determination which are usually carried out in practice.

The requirements which are demanded of such control or calibration sera in clinical-chemical routine operations include:

in the case of control sera, the concentration ranges of the individual measurement parameters must be known precisely and, in the case of calibration sera, a precise, known concentration of the particular measurement parameter must be maintained;
the concentrations must lie in the medically relevant measurement range (normal or pathological);
the handling of these sera must be simple; and
the sera must have a storage stability which is as long as possible.

Control and calibration sera have been known for some time for lipid diagnosis. It is a disadvantage of these known sera that they are individually only suitable for quite definite lipid parameters. A control serum or calibration serum which contains all or at least all relevant parameters for lipid diagnosis is hitherto unknown.

Thus, for example, control sera for the determination of HDL cholesterol and the apolipoproteins are commercially available. A quality control or calibration serum which, besides these parameters, also contains LDL cholesterol in sufficient concentration has hitherto not been described.

However, it is precisely this parameter which is of special importance for diagnosis. As long ago as 1954, it had been found, by separation of the lipoproteins in an ultracentrifuge that, in the case of the presence of coronary heart diseases, high LDL concentrations were frequently measured. Jenkins et al. (Brit. Med. Journal, 2, 388 et seq., 1978) were able to show a connection between the severity of a coronary disease and the level of the LDL cholesterol concentration. Although the importance of the LDL determination has already been known for a long time, hitherto there has been no control or calibration serum which contains the parameters relevant for lipid diagnosis, especially LDL cholesterol, with the necessary stability and the necessary concentration in a single available form. Therefore, there is still a need for a control or calibration serum which can be used for the determination of each parameter which is important for lipid diagnosis.

It is an object of the present invention to fulfil this need.

Thus, according to the present invention, there is provided a control or calibration serum for lipid diagnosis, wherein it contains the parameters relevant for lipid diagnosis in the normal or pathological concentration range in a single, storage-stable form.

The control or calibration serum according to the present invention preferably contains the parameters important for fat metabolism, i.e. total cholesterol, HDL cholesterol, LDL cholesterol and triglycerides, as well as the three apolipoproteins A1, A2 and B. In addition, it can also contain $\beta$-lipoproteins, phospholipids and lecithin. At least the apolipoproteins A1, A2 and B are components of a control or calibration serum according to the present invention. A control or calibration serum is especially preferred which is at least suitable for the parameters HDL cholesterol, LDL cholesterol and the apolipoproteins A1, A2 and B.

In a control serum, the concentration ranges of the individual parameters vary within the limits given in the following Table 1, it being necessary to differentiate between a control serum for the normal range and for the pathological range.

TABLE 1

Concentration ranges for the individual parameters of a control serum

| substance | normal range (mg./dl.) | pathological range (mg./dl.) |
| --- | --- | --- |
| total cholesterol | 140–240 | 220–320 |
| HDL cholesterol | 50–70 | 20–50 |
| LDL cholesterol | 90–150 | 140–250 |
| triglycerides | 70–110 | 120–200 |
| Apo A1 | 90–140 | 50–90 |
| Apo A2 | 25–50 | 20–40 |
| Apo B | 80–120 | 110–170 |
| $\beta$-lipoproteins | 350–650 | |
| phospholipids | 150–300 | |
| lecithin | 120–220 | |

The calibration sera contain the individual parameters in a quite definite concentration. This concentration can, of course, vary from batch to batch within certain limits. The values usually lie within the range given in the following Table 2:

TABLE 2

Concentration ranges for calibration sera

| substance | concentration (mg./dl.) |
| --- | --- |
| apolipoprotein A1 | 100–130 |
| apolipoprotein A2 | 35–50 |
| apolipoprotein B | 85–115 |
| total cholesterol | 180–280 |
| HDL cholesterol | 40–80 |
| LDL cholesterol | 120–180 |
| triglycerides | 90–130 |

Not only the control serum but also the calibration serum according to the present invention can contain additional adjuvant materials, for example clarification agents, stabilising agents, detergents and preserving agents. As clarification agent, there can be used, for example, pentaerythritol and as stabilising agents there are especially suitable sugars, particularly saccharose, which can be added in an amount of from 4 to 12% by weight. As preserving agents, there can, in particular, be used azides, merthiolate and antibiotics. However, other known adjuvant materials can also be used.

For the preparation of the control or calibration sera according to the present invention, fresh human serum is used as starting material. It is also possible to use fresh human plasma which is worked up to give human serum. The human plasma or serum should not be more than 5 to 10 days old. Human plasma or human serum which, immediately after it has been obtained, has been deep-frozen and has been temporarily stored in this form can also be used for the preparation of the product according to the present invention. After thawing, the human plasma is then worked up to give human serum. The desired parameter concentration is adjusted in the raw material in the usual manner. This can take place by concentration of the solution if a higher concentration of the component materials is to be achieved. If it is necessary to lower the parameter concentration, then a dilution agent, for example an appropriate buffer solution, is added thereto. The adjuvant materials, for example 4 to 12% by weight of a stabilising agent, such as saccharose, are added thereto. Thereafter, there takes place a filtration through a membrane filter ($\leq 2$ μm. mesh size) for reducing the amount of germs. The solution thus obtained is filled in the desired amount into ampoules of appropriate size (1 to 5 ml.) and preferably lyophilised. Before use, this lyophilisate is reconstituted with an aqueous medium and preferably with distilled water.

The control or calibration serum according to the present invention can also be obtained on the basis of bovine serum albumin (BSA). For this purpose, it is necessary to adjust the desired parameter concentration by the addition of appropriate concentrates. As such concentrates, there are especially suitable HDL cholesterol and LDL cholesterol concentrates of human origin, triglyceride-rich egg yolk extracts and the like. The bovine serum albumin, preferably in the form of an aqueous solution (6 to 10% by weight), is mixed with the concentrates. By variation of the mixing ratios, there can be obtained, in desired manner, "normal" and "pathological" concentrations of the lipid parameters.

In a lyophilised state, the control or calibration serum according to the present invention is storage stable for at least 2 years at 4° C. It is outstandingly suitable as a quality control and calibration serum for HDL cholesterol, LDL cholesterol and the three apolipoproteins A1, A2 and B. In particular, according to the present invention, the three apolipoproteins A1, A2 and B can be so enriched in sufficiently high concentrations that it is readily possible to produce calibration curves not only for the relevant pathological range but also for the physiological range.

The following Examples are given for the purpose of illustrating the present invention:

EXAMPLE 1

Quality Control Serum for Lipid Control (Normal)

600 ml. fresh human plasma with a protein content of 5.0 g./dl. is worked up to give human serum by recalcification and separation of the coagulum. The serum is concentrated to one half of its original volume (about 300 ml.) and the protein concentration thus simultaneously brought to 7.7 g./dl.

After dialysis (3×5 hours) against, in each case, a 30 fold volume of a buffer of pH 8.0 (the buffer contains 4.5 mM/l. potassium chloride, 105 mM/l. sodium chloride, 1 mM/l. magnesium sulphate heptahydrate, 1 mM/l. disodium hydrogen phosphate dihydrate, 15 mM/l. sodium bicarbonate and 17.5 mM/l. sodium acetate), the serum is filtered for the reduction of the amount of germs (EKS I filter of Schleicher & Schüll). The yield of serum after this filtration is 250 ml. 10% by weight of saccharose (10 g./100 ml.) are dissolved therein and the serum is filtered through membrane filters with a mesh size of $\leq 0.2$ μm. Subsequently, the serum is filled into ampoules in 3 ml. portions and lyophilised.

When the lyophilisate so obtained is reconstituted with 3 ml. of double distilled water, the reconstituted serum contains the following components in the given concentrations:

| total cholesterol | 231.2 mg./dl. |
|---|---|
| HDL cholesterol | 65.7 mg./dl. |
| LDL cholesterol | 144.7 mg./dl. |
| triglycerides | 106.1 mg./dl. |
| Apo A1 | 105.6 mg./dl. |
| Apo A2 | 41.3 mg./dl. |
| Apo B | 99.1 mg./dl. |
| β-lipoproteins | 556.0 mg./dl. |
| phospholipids | 276.0 mg./dl. |
| lecithin | 201.0 mg./dl. |

EXAMPLE 2

Quality Control Serum for Lipid Control (Pathological)

500 ml. of fresh human plasma with a protein content of 5.7 g./dl. are worked up to serum in the manner described in Example 1. The serum is concentrated to 225 ml. and, after concentration and dialysis (as in Example 1 ), has a protein content of 9.8 g./dl. For reducing the amount of germs, the serum is filtered through an EKS I filter (Schleicher & Schüll). After this filtration, the yield of serum is 200 ml.

For increasing the LDL cholesterol and the apolipoprotein B concentration, the 200 ml. of serum are mixed with 95 ml. of a human LDL cholesterol concentrate (preparation see below).

10% by weight of saccharose (10 g./100 ml.) are dissolved therein and the serum is filtered through a membrane filter of a mesh size of $\leq 0.2$ μm. Subsesequently, the serum is filled in 3 ml. portions into ampoules and lyophilised.

When the lyophilisate so obtained is reconstituted with 3 ml. of double distilled water, the reconstituted serum contains the following components in the given concentrations:

| total cholesterol | 314.0 mg./dl. |
|---|---|
| HDL cholesterol | 47.8 mg./dl. |
| LDL cholesterol | 234.9 mg./dl. |
| triglycerides | 157 3 mg./dl. |
| Apo A1 | 85.7 mg./dl. |
| Apo A2 | 32.0 mg./dl. |
| Apo B | 165.2 mg./dl. |
| β-lipoproteins | not measured |
| phospholipids | not measured |
| lecithin | not measured |

For the preparation of the human LDL cholesterol concentrate, human plasma is worked up in known manner to give human serum and dialysed against the buffer described in Example 1. LDL cholesterol is precipitated out from 2500 ml. of the human serum thus obtained with a polyvinyl sulphate solution (c=3 g./l.; amount 500 ml.) and the sediment is taken up and dissolved in 100 ml. of a 0.05% EDTA solution with 4.6% sodium chloride (pH 7.0). The yield is 135 ml. This solution is dialysed overnight against 10 liters of 3M aqueous potassium chloride solution with 0.05% EDTA (pH 7.0) and centrifuged off from the precipitate formed. The 110 ml. of supernatant are dialysed against 10 liters of a solution of 120 mMol/l. sodium chloride and 25 mMol/l. sodium bicarbonate for the removal of the potassium chloride. The yield is 130 ml. with the following analyte concentrations:

| | |
|---|---|
| total cholesterol | 1004.0 mg./dl. |
| HDL cholesterol | 4.3 mg./dl. |
| LDL cholesterol | 902.0 mg./dl. |

This human LDL cholesterol concentrate is stabilised with 0.1% by weight of sodium azide and stored at 4° C. until used.

EXAMPLE 3

Calibration Serum for the Apolipoproteins A1, A2 and B 500 ml. of fresh human plasma with a protein content of 5.6 g./dl. are worked up as described in Example 1 to give serum and concentrated to such an extent (to about 270 ml.) that a protein content of 9.0 g./dl. is obtained. There follow the dialysis and filtration through an EKS-I filter as described in Example 1. The serum yield is 220 ml. 10% by weight of saccharose (10 g./100 ml.) are dissolved therein and the serum is filtered through a membrane filter of 0.2 μm. mesh size. Subsequently, the serum is filled into ampoules in 1 ml. portions and lyophilised. After reconstitution of the lyophilisate with 1 ml. of double distilled water, it contains the following components in the given concentrations:

| | |
|---|---|
| apolipoprotein A1 | 127.0 mg./dl. |
| apolipoprotein A2 | 47.0 mg./dl. |
| apolipoprotein B | 110.0 mg./dl. |

It will be understood that the specification and examples are illustrative but not limitative of the present invention and that other embodiments within the spirit and scope of the invention will suggest themselves to those skilled in the art.

What is claimed is:

1. A control or calibration system for lipid diagnosis containing parameters relevant for lipid diagnosis in the normal or human pathological concentration range in a single storage-stable form, said parameters comprising 140–320 mg/dl total cholesterol, 20–80 mg/dl HDL cholesterol, 90–250 mg/dl LDL cholesterol, 70–200 mg/dl triglycerides, 50–140 mg/dl apolipoprotein A1, 20–50 mg/dl apolipoprotein A2 and 80–170 mg/dl apolipoprotein B.

2. The control or calibration serum of claim 1, wherein said parameters comprise 40–80 mg/dl HDL cholesterol, 120–180 mg/dl LDL cholesterol, 100–130 mg/dl apolipoprotein A1, 35–50 mg/dl apolipoprotein A2 and 85–115 apolipoprotein B.

3. The control or calibration serum of claim 1 in lyophilised form.

4. The control or calibration serum of claim 1 wherein said parameters comprise 100–130 mg/dl apolipoprotein A1, 35–50 mg/dl apolipoprotein A2, 85–115 mg/dl apolipoprotein B, 180–280 mg/dl total cholesterol, 40–80 mg/dl HDL cholesterol, 120–180 mg/dl LDL cholesterol, 90–130 mg/dl triglycerides.

5. A process for the preparation of a control or calibration serum containing parameters in the normal or human pathological concentration range, which parameters comprise predetermined amounts of apolipoprotein A1, A2 and B; total cholesterol; HDL cholesterol; LDL cholesterol and triglycerides; in the normal or human pathological concentration range, said process comprising:
   obtaining as starting material, fresh blood serum, blood serum which has been fresh frozen and freshly thawed, or blood serum from plasma which has been freshly frozen and freshly thawed;
   determining the amounts of the parameters in said serum;
   adjusting the parameter concentrations into said predetermined amount by adding an LDL cholesterol concentrate, an HDL cholesterol concentrate and a triglyceride-rich egg yolk extract; and;
   working up the adjusted serum into storage stable form.

6. The process of claim 5 wherein the starting material is human blood plasma or serum.

7. The process of claim 5 wherein the starting material is bovine serum albumin.

8. The process of claim 5, further comprising adding, as an adjuvant, 4 to 12% by weight of saccharose.

9. The process of claim 5 wherein the serum is worked-up into storage stabile form by lyophilizing the serum.

* * * * *